United States Patent [19]

Gehrman et al.

[11] Patent Number: 4,525,351

[45] Date of Patent: Jun. 25, 1985

[54] LIQUID ADHERENT DISINFECTANT COMPOSITIONS FOR TOPICAL APPLICATION AND METHOD OF PREPARATION

[75] Inventors: Sybil H. Gehrman; Randolph S. Porubcan, both of West Allis, Wis.

[73] Assignee: Chr. Hansen's Laboratory, Inc., Milwaukee, Wis.

[21] Appl. No.: 457,212

[22] Filed: Jan. 11, 1983

[51] Int. Cl.$^3$ .................. A01N 63/02; C12P 7/56
[52] U.S. Cl. .................... 424/95; 252/106; 426/2; 426/43; 435/853; 435/854
[58] Field of Search .............. 424/177, 95, 315; 435/139, 885, 853, 854, 857, 41, 68, 11; 426/2, 42, 43; 252/106

[56] References Cited

U.S. PATENT DOCUMENTS

| | | | |
|---|---|---|---|
| 3,262,884 | 7/1966 | Myers | 252/106 |
| 3,689,640 | 9/1972 | Shahani et al. | 435/854 |
| 4,199,564 | 4/1980 | Silver et al. | 424/81 |

FOREIGN PATENT DOCUMENTS

| | | | |
|---|---|---|---|
| 0113708 | 9/1981 | Japan | 435/885 |
| 787184 | 10/1955 | United Kingdom | 426/43 |

OTHER PUBLICATIONS

Auclair, Journal of Dairy Research, vol. 20, 1953, pp. 323-336.

*Primary Examiner*—Sam Rosen
*Assistant Examiner*—William J. Herald

[57] ABSTRACT

A liquid adherent disinfectant composition for topical application comprises an aqueous acidic suspension of previously coagulated casein containing an aliphatic sulfate detergent as the effective agent for solubilizing the casein and converting it to a mucilaginous condition. The preparation also preferably contains glycerin and Lactobacillus-elaborated antibiotic-like factors. The composition can be prepared by fermenting a non-fat dry milk culture medium with harmless lactic acid-producing bacteria, such as *Lactobacillus acidophilus*, until the casein coagulates, thereafter mechanically dispersing the coagulated casein and solubilizing it with the aliphatic sulfate detergent. The resulting disinfectant composition can be used as a teat dip for preventing mastitis in cattle, or for other topical disinfecting purposes with domestic animals. The compositions adhere to the areas to which they are applied while being readily removable by water washing.

12 Claims, No Drawings

LIQUID ADHERENT DISINFECTANT COMPOSITIONS FOR TOPICAL APPLICATION AND METHOD OF PREPARATION

BACKGROUND AND PRIOR ART

The field of this invention is liquid disinfectant compositions particularly disinfectant compositions for application to domestic animals. A particular field of use is for prevention or treatment of mastitis in cattle.

The economic loss in the United States caused by mastitis infection of dairy cattle has been estimated to be in excess of two billion dollars annually. For a discussion of the magnitude of this problem see *Current Concepts of Bovine Mastitis,* 2nd edition, 1973, Published by National Mastitis Council, Inc., 30F Street NW, Washington, D.C. 20001. For prevention or control of mastitis, a wide variety of teat dip solutions have been applied to the udders of cattle, and many commercial preparations are presently being marketed in the United States. As the principal disinfecting agent, these preparations usually contain iodophor, sodium hypochloride, chlorhexidine, or mixtures thereof. Teat dips containing iodophor at concentrations of from 0.5 to 1% have been favored.

Since a number of bacterial pathogens cause or contribute to mastitis, the disinfecting agent must function bacteriostatically or bactericidally against a broad spectrum of bacteria. Various antibiotics have been used in preparations for the prevention or treatment of mastitis, but many antibiotics do not have a sufficiently broad spectrum of acitivity. A further limitation is that antibiotic residues cannot be present in the milk if it is to be sold.

Heretofore no fully satisfactory liquid composition has been developed for the prevention, control, or treatment of mastitis. Ideally, such a preparation would be easy to apply, non-irritating to the teats and udders, bacteriostatically and/or bactericidally effective against the pathogens associated with mastitis, adherent to the teat surfaces to which it is applied in the intervals between milking or treatment, and yet easily and completely removable prior to milking.

SUMMARY OF INVENTION

During the course of the experimental work leading to the present invention, it was discovered that a highly desirable ingredient of a liquid teat disinfecting composition comprises casein which has previously coagulated, such as by fermentation with a lactic acid-producing bacteria, and thereafter mechanically dispersed and solubilized with an aliphatic sulfate detergent such as an alkali metal or ammonium salt of dodecyl sulfate. It was found that the dispersed and solubilized particles of the casein acquire a mucilaginous character due to the action of the detergent thereon. This provides the disinfectant composition with a sticky character which makes it adhere to the teats and udders after application thereto, while at the same time being readily and completely removable by water washing when desired. The composition can be at an acid pH inhibitory to the growth of bacteria, and the composition may contain additional antimicrobial agents. In particular, it may contain antibiotics elaborated by the fermentation of a nonfat dry milk-containing culture medium with an antibiotic-producing strain of Lactobacillus, such as *Lactobacillus acidophilus*.

The compositions may also contain an emollient such as glycerin as presently used in commercial teat dip formulations. In order to produce the most stable disinfectant compositions in accordance with the present invention, it has been found to be important to add the emollient following the solubilization of the casein with the detergent.

DETAILED DESCRIPTION

In preparing the disinfecting compositions of the present invention, substantially undenatured casein dispersed in water is subjected to coagulation by lowering the pH of the aqueous medium to a pH below the isoelectric pH of the casein. This may be accomplished by the addition of an acid such as lactic acid to the medium, or by fermenting the medium with "Lactic Acid Bacteria".

As used in the present application the term "Lactic Acid Bacteria" refers to the broad class of harmless lactic acid-producing bacteria. In general, such bacteria possess the ability to ferment simple carbohydrates such as lactose or glucose, with lactic acid being at least one, and usually the most abundant, of the fermentation products. Among such Lactic Acid Bacteria are the following: *Streptococcus lactis, Streptococcus cremoris, Streptococcus diacetylactis, Streptococcus thermophilus, Lactobacillus bulgaricus, Lactobacillus acidophilus, Lactobacillus helveticus, Lactobacillus bifidus, Lactobacillus casei, Lactobacillus lactis, Lactobacillus plantarum, Lactobacillus delbrueckii, Lactobacillus thermophilus, Lactobacillus fermentum,* and *Pediococcus cerevisiae.* The aqueous dispersion of casein may be in the form of skim milk, but is preferably reconstituted milk formed from nonfat dry milk solids (NFDM). The medium may have a milk solids nonfat concentration of 6 to 16% by weight, such as, preferably, 10 to 14% solids. On a casein basis, the medium may correspondingly contain from 1.5% to 4.0% casein by weight. The corresponding preferred range on the same basis is from about 2.5% to 3.5% casein.

After the casein has been coagulated by pH reduction, such as by the addition of or the in situ formation of lactic acid, the resulting coagulum is mechanically disintegrated. For example, the medium containing the coagulum may be processed in a blender or an emulsifier wherein sufficient shearing force is generated to break up the coagulum into small particles of casein. Sonication may also be used. Following disintegration of the casein coagulum, a relatively large amount of an aliphatic sulfate detergent is dissolved in the aqueous medium.

The aliphatic sulfate salt, for example, may be sodium, potassium, or ammonium aliphatic sulfates, or mixtures thereof, containing from 10 to 18 carbons in their aliphatic groups. The preferred detergents are the aliphatic sulfates which are composed primarily of dodecyl sulfate ($C_{12}$ aliphatic group). Lesser amounts of $C_{14}$ and $C_{16}$ aliphatic sulfonates may be present in admixture with the dodecyl sulfate. A sufficient amount of the aliphatic sulfate detergent should be used so that it effectively solubilizes the dispersed casein particles and converts the casein to a translucent, mucilaginous condition. For example, the selected amount of detergent may be within the range from 1.8 to 3.4 parts by weight of active detergent per part of casein. Preferably, the amount of detergent will range from about 2.4 to 3.2 parts by weight of active detergent per part of casein.

After the casein has been solubilized and the suspension thereof stabilized with the detergent, other additives may be readily incorporated in the disinfectant composition. For example, it is preferred to mix a water-soluble emollient into the composition, such as glycerin, or other emollient polyhydroxy alcohol like propylene glycol or sorbitol. The amount of the emollient can range from 5 to 15% by weight based on the total weight of the composition. Where glycerin is added, an amount of from about 9 to 13% is preferred.

Other additives which can be incorporated include auxillary disinfecting agents, such as sorbic acid. For example, from 0.1 to 0.3% by weight sorbic acid may be included based on the weight of the composition. Moreover, other antimicrobial substances may be incorporated, such as particularly the anitibiotic-like substances produced by certain strains of Lactobacillus, including particularly *Lactobacillus acidophilus* and/or *Lactobacillus bulgaricus*. With the preferred method of preparing the disinfectant compositions, such antibiotic is produced in situ during the fermentation, which also produces the lactic acid required for coagulating the casein.

PREFERRED METHOD OF PREPARATION

In a preferred method of preparation of the disinfectant compositions of this invention, a culture medium is first prepared from water and nonfat dry milk solids (NFDM). The medium can contain from 6 to 16% by weight of NFDM, but preferably contains from 10 to 14% about 2.5 to 3.5% casein) such as a typical concentration of about 12% NFDM (about 3% casein). The pH of the medium will be at a pH above the isoelectric pH of the casein. For example, the starting pH may be the natural pH of reconstituted NFDM, such as a pH within the range from 6.0 to 7.0.

The Lactic Acid Bacteria may be added as a viable freeze-dried culture, or as a liquid culture which has been stored in frozen condition, or in the form of a bulk starter. For the purpose of the present application, a freeze-dried culture may be used directly as a starter at a concentration of 0.5% or less, or a bulk starter culture can be added in amounts of from 1% to 2% by weight based on the medium.

Preferably, the Lactic Acid Bacteria is an antibiotic-producing strain of Lactobacillus. For example, the inoculant may be a suitable strain of *Lactobacillus acidophilus* and/or *Lactobacillus bulgaricus*. Strains of these bacteria have been shown to produce antibiotic factors, which have been referred to in the literature as "Acidolin" or "Acidophilin". See Shahani, et al, *Cultured Dairy Products Journal*, 11(4), 14–16, (1976); Shahani, et al, *Cultured Dairy Products Journal*, 12(2), 8–11 (1977); Hamdan, et al, *The Journal of Antibiotics*, 27(8) 631–636 (1974); and Shahani, et al, U.S. Pat. No. 3,689,640 (1972).

The fermentation is carried out by incubating the inoculated medium under temperature conditions favoring the growth of the bacteria, such as temperatures of about 30°–37° C. The fermentation is continued until the casein precipitates as a coagulum, and thereafter it is continued to promote the elaboration of the antibiotic, if the bacteria are antibiotic-producing Lactobacilli. As described in the Shahani, et al references cited above, "overincubation" promotes the antibiotic production from *Lactobacillus acidophilus* and/or *bulgaricus*. For example, the pH may have dropped sufficiently to coagulate the medium in from 12 to 16 hours, but for overinculation, the fermentation may be continued to 24 to 48 hours. Usually, a total fermentation time for the coagulation and the antibiotic production of 48 hours gives good results.

At the conclusion of the fermentation, the pH will be at a pH below the isoelectric point of casein, such as a pH in the range of about 3.5 to 4.5. Typical fermentation completion pH's are around 3.8 to 4.2. The pH can be adjusted as required with lactic acid or ammonium hydroxide to give a final product pH of 3.8 to 4.6, which is inhibitory to the growth of bacterial pathogens. A product pH of around 4.4 (4.3–4.5) has been particularly desirable.

Following completion of the fermentation, the medium contains the casein coagulum, the bacterial cells, lactic acid produced in the fermentation, and, if produced, any antibiotic factors. The fermented medium is then subjected to mechanical disintegration to break up and disperse the casein in the form of fine particles. For example, the fermented medium may be processed in an emulsifier or blender, or passed through a pump producing high shear. Following the dispersion of the casein or concurrently therewith, an aliphatic sulfate detergent, as described above, is dissolved in the aqueous phase of the medium. The amounts to be used are as described above. For example from 2.4 to 3.2 parts by weight of active detergent may be present per part of casein. Al already described, the detergent, such as sodium or ammonium lauryl sulfate, solubilizes the casein particles, stabilizes the suspension thereof, and converts the casein to a sticky, tacky form, which is referred to herein as "mucilaginous". The detergent also provides an antimicrobial action. Following the addition of the detergent and the solubilization of the casein, other additives, such as glycerin may be introduced, as described above.

The resulting compositions are useful for topical application to animals, and particularly for use in preventing or treating mastitis in cattle. For example, the compositions may be used as a teat dip for preventing mastitis. On application to the teats and udders, the applied composition will partiallly dry, water being evaporated therefrom. The residual soft film of the composition, which will still contain some water, will be adherent, although it can be readily removed prior to the next milking by washing the teats and udders with water.

The compositions may also be used in the treatment of mastitis infection, such as by intramammary infusion. Where the composition has been prepared as preferred, there will be no need to discard milk from the infused animals for long periods, such as 72 to 96 hours following the treatment.

The compositions of this invention are also susceptible to other uses, such as whereever a topical antimicrobial is desired. For example, the compositions can be used as a foot dip with feed lot cattle. Also, the compositions may be used for the treatment of wounds or sores on domestic animals.

This invention is further illustrated by the following examples and test results.

EXAMPLE I

A 1,000 gallon batch of culture medium is prepared by reconstituting 1,032 pounds of nonfat dry milk solids (NFDM) with 7,573 pounds of water. This gives a medium with a 12% NFDM concentration. The reconstituted milk is pasteurized for one hour at 90° C., or otherwise pasteurized in accordance with known practices. A bulk starter culture is prepared for inoculation of the medium. Sterilized 12% reconstituted NFDM is inoculated at the 1% level with a freeze-dried culture of *Lactobacillus acidophilus*, such as the strain ATCC No. 4356, American Type Culture Collection, Rockville, Maryland. Preferably, however, the modification of strain ATCC No. 4356 is used, Hansen's LA-1, Chr. Hansen's Laboratory, Milwaukee, Wis. Alternatively, Hansen's strain LA-2 may be used. Strain LA-2 has morphological and biochemical characteristics of both *Lactobacillus acidophilus* and *lactis*. The strains ATCC 4356, LA-1, and LA-2 produce the antibiotic-like factors referred to in the literature as "Acidolin" and/or "Acidophilin". The starter culture can be incubated at 37° C. for 16 hours to produce a mother culture. The foregoing cultures are commercially available from Hansen's, and have been publicly deposited on an unrestricted basis in the permanent collection of microorganisms of The Northern Regional Research Laboratories, U.S.D.A., Peoria, Ill. under Nos. NRRL B-15260 for LA-1 and NRLL B-15261 for LA-2.

Five hundred gallon aliquots of the culture medium prepared as described above are inoculated with 1% of the mother culture. Inoculated medium is fermented for 48 hours at 37° C. This "overincubation" maximizes the production of the Acidolin-Acidophilin factors. On completion of the fermentation the pH is usually about 3.75–4.15, and the casein of the NFDM is in the form of a coagulum.

In one presently preferred procedure, two 500 gallon aliquot cultures are prepared by the overincubation procedure described, one being inoculated with the strain LA-1 and the other with the strain LA-2. Following completion of the fermentation, the two cultures are mixed to produce a 1,000 gallon product mixture. This product mixture containing the coagulated casein is then subjected to disintegration by being processed in an emulsifier or blender. The mixing is continued until the coagulum is broken up, the particles dispersed, and a mixture with smooth consistency is obtained.

Following the disintegration of the coagulum, under slow, continuous mixing 834 pounds of a sodium lauryl sulfate detergent is added gradually to the product mixture. This provides a level of about 10% by weight of the detergent based on the total product mixture. The preferred detergent is one composed predominantly of sodium lauryl sulfate, such as "Texapon K-12" of Henkel Chemical Specialties, Hoboken, N.J. This product is in the form of a white powder and contains about 89-90% active detergent.

When the detergent is effectively dissolved, 0.2% sorbic acid (17.2 pounds) is added and mixed into the product. Finally, 11% glycerin (917 pounds) is added and mixed into the product to produce the final formulation. The product will have a pH of from 4.2 to 4.5. Preferably when required the pH is adjusted to 4.4 with lactic acid or ammonium hydroxide. The product is ready for use as a teat dip for prevention of mastitis, or for other topical disinfectant uses for domestic animals.

EXAMPLE II

A disinfectant composition prepared as described in Example I was tested for in vitro growth inhibition of mastitis pathogens, including *Staphylococcus aureus, Streptococcus agalactiae, Streptococcus dysgalactiae,* and *Streptococcus uberis*. Excised teat assays were conducted as follows: Brain Heart Infusion tubes were inoculated with each of the above bacterial pathogens. Tubes were incubated and serial dilutions made so that a challenge dip contained at least $1 \times 10^8$ colony forming units per ml for each bacterial strain tested. Each assay contained 30 excised teats for: 10 negative controls, 10 dipped with 1% iodophor as a positive control, and 10 dipped with the Example I composition. All teats were dipped to a depth of 15 mm in the bacterial challenge suspension and allowed to drain. Teats dipped with the positive control and the Example I composition were immersed to a depth of 30 mm and allowed to drain.

Surviving bacteria were removed from the skin of excised teats by rinsing with 10 ml of a standard culture broth, and collected in sterile vials. The liquid was surface plated on duplicate plates of selective media. The bacteria were plated on suitable standard plate culture media. Plates were incubated at 37° C. for 24 hours. Following incubation bacteria were enumerated, bacterial log reductions determined and compounds compared.

Results of the excised teat assays are presented in Table A. Data are presented in terms of log reduction and percent kill. Log reduction equals the number of bacteria on negative control teats ($\log_{10}$) — the number of bacteria on teats dipped with experimental compounds ($\log_{10}$). Percent kill was derived by dividing log reduction by the log of negative control teats multiplied by 100.

TABLE A

| | Bactericidal Assays by Excised Teat Test | | | |
|---|---|---|---|---|
| | 1% iodophor | | Ex. I Composites | |
| Mastitis Pathogen | Log Reduction | % Kill | Log Reduction | % Kill |
| *Staph. aureus* | 5.52 | 72.7 | 5.50 | 72.3 |
| *Strep. agalactiae* | 6.40 | 96.5 | 6.63 | 100 |
| *Strep. dysgalactiae* | 6.48 | 94.9 | 6.52 | 95.5 |
| *Strep. uberis* | 5.53 | 94.3 | 5.56 | 95.0 |

EXAMPLE III

The coagulated culture medium is prepared according to the preferred procedure described in Example I, and disintegrated. To the resulting 1,000 gallon product mixture, there is added 2,500 pounds of aqueous ammonium lauryl sulfate (27.5-28.5% active detergent). A suitable aqueous detergent with the indicated activity is Standapol A, Henkel Corporation, Chemical Specialties Division, Teaneck, N.J. After thorough mixing, the culture/detergent blend has a lower viscosity than the culture/detergent blend of Example I because of the additional water added with the ammonium lauryl sulfate. The viscosity is increased to a viscosity similar to that of the culture/detergent blend of Example I by adding 47.1 pounds of Cocamide DEA. Alternatively, other viscosifier additives can be used, such as hydrocolloid viscosifiers.

The sorbic acid (17.2 pounds) is then added and mixed into the product. Finally, 11% glycerin (917 pounds) is added and mixed into the product to produce the final formulation. The pH is adjusted, as required, to a standardized pH of 4.4 by adding lactic acid or ammonium hydroxide.

The product prepared with the ammonium lauryl sulfate instead of the sodium lauryl sulfate has the advantage of greater temperature stability. It is therefore preferred where it is to be stored or used at temperatures below 50° F., such as temperatures in the range of 32°-45° F. At these temperatures the sodium lauryl sulfate product of Example I will form a precipitate, which will settle to the bottom of the preparation. However, on warming the preparation to a temperature above 50° F., such as 60°–80° F., a stable suspension can be readily reformed by gentle shaking of the product.

EXAMPLE IV

Sodium lauryl sulfate and ammonium lauryl sulfate products are prepared as described in Examples I and II, except that *Streptococcus cremoris* is substituted as the lactic acid-producing bacteria for the *L. acidophilus* and/or *L. bulgaricus*. A mother culture is prepared as described in Example I, which is then used to inoculate 1,000 gallons of the 12% NFDM culture medium, as described in Example I. The fermentation is carried out at a temperature of 30° C. for 16 hours. The milk solids are coagulated by the lactic acid produced in the fermentation. The preparation of the product is then completed, as described in Example I for a product containing sodium lauryl sulfate, or as described in Example III for ammonium lauryl sulfate.

EXAMPLE V

A 1,000 gallon batch of 12% NFDM is prepared as described in Example I. Lactic acid is added to the medium in a sufficient amount to lower the pH to 4.0–4.1. No bacterial culture is added and no fermentation is used. The added lactic acid coagulates the milk protein. The resulting coagulum-containing medium is then processed as described in Example I to prepare a product containing sodium lauryl sulfate, or as described in Example III to obtain a product containing ammonium lauryl sulfate. These products are suitable for use as adherent disinfectant compositions for topical application. However, they are not as smooth and homogeneous as the products of Examples I and III.

We claim:

1. A method of preparing a liquid adherent disinfectant mixture, comprising:
   (a) preparing a fermentable culture medium from water and nonfat dry milk solids (NFDM), said medium containing from 6 to 16% by weight of NFDM and from 1.5 to 4.0% casein;
   (b) inoculating the culture medium with a lactic acid producing fermentation culture;
   (c) fermenting said inoculated medium with the production of lactic acid at least until the casein precipitates as a coagulum; and
   (d) thereafter mechanically disintegrating the casein coagulum in the medium to form fine particles thereof, and dissolving in said medium from 1.8 to 3.4 parts by weight of active detergent per part of disintegrated casein, said detergent being selected from the class consisting of the sodium; potassium and ammonium aliphatic sulfate detergents and mixtures thereof wherein the aliphatic groups contain from 10 to 16 carbons, said disintegrated casein being mixed with said detergent and being effective to disperse and solubilize said disintegrated casein, whereby said final mixture is in a sticky adherent condition.

2. The disinfectant mixture produced by the method of claim 1.

3. The method of claim 1 in which said aliphatic sulfate detergent is a sodium aliphatic sulfate detergent composed principally of sodium dodecyl sulfate.

4. The method of claim 1 in which said aliphatic sulfate detergent is composed principally of ammonium dodecyl sulfate.

5. The disinfectant mixture produced by the method of claim 3.

6. The disinfectant mixture produced by the method of claim 4.

7. The method of claim 1 in which said culture comprises strains selected from the class of Lactobacilli consisting of *Lactobacillus acidophilus, Lactobacillus bulgaricus, Lactobacillus lactis,* and mixtures thereof.

8. The disinfectant mixture produced by the method of claim 7.

9. A method of preparing a liquid adherent disinfectant mixture, comprising:
   (a) preparing a culture medium from water and nonfat dry milk solids (NFDM) said medium containing at least 10% but not over 16% by weight of NFDM and from 2.5 to 3.5% by weight of casein;
   (b) inoculating the culture medium with a Lactobacillus fermentation culture;
   (c) fermenting said inoculated culture with the production of lactic acid at least until the pH drops to a pH at which the casein precipitates as a coagulum; and
   (d) thereafter mechanically disintegrating the casein coagulum in the medium to form fine particles thereof, and dissolving in said medium from 2.4 to 3.2 parts by weight of active detergent per part of casein said detergent being an aliphatic sulfate detergent composed principally of dodecyl sulfate and said detergent being effective to solubilize said disintegrated casein, whereby said final mixture is in a sticky adherent condition.

10. The disinfectant mixture produced by the method of claim 9.

11. The method of claim 9 in which following step (d) glycerin is mixed into the detergent-containing medium in an amount of from 5 to 15% by weight based on the total composition.

12. The disinfectant mixture produced by the method of claim 11.

* * * * *